United States Patent [19]
Elbrecht et al.

[11] Patent Number: 5,872,150
[45] Date of Patent: Feb. 16, 1999

[54] TREATMENT OF PROSTATE DISEASE WITH A NONSTEROIDAL ANTI-ANDROGENIC COMPOUND

[75] Inventors: Alex Elbrecht, Watchung; Jeffrey H. Toney, Basking Ridge, both of N.J.

[73] Assignee: Merck & Co., Inc., Rahway, N.J.

[21] Appl. No.: 806,944

[22] Filed: Feb. 26, 1997

Related U.S. Application Data

[60] Provisional application No. 60/012,638, Mar. 1, 1996.
[51] Int. Cl.$^6$ .................. A61K 31/16; G01N 33/574; C12N 5/00
[52] U.S. Cl. .................. 514/563; 435/7.23; 435/325; 435/352; 435/384
[58] Field of Search .................. 514/563; 435/7.23, 435/325, 352, 384

[56] References Cited

U.S. PATENT DOCUMENTS

| 3,953,290 | 4/1976 | Uthne et al. | 435/384 |
| 5,130,462 | 7/1992 | Slusarchyk | 558/58 |

OTHER PUBLICATIONS

Marugo et al., J. Steroid Biochem. Molec. Biol., vol. 42, No. 5, pp. 547–554 (1992), "Effects of dihydrotestosterone and hydroxyflutamide on androgen receptors in cultured human breast cancer cells (EVSA–T)".

Lippman et al., Cancer Research, vol. 36, pp. 4610–4618 (1976), "The effects of androgens and antiandrogens on hormone–responsive human breast cancer in long–term tissue culture".

Norris et al., Nature, vol. 248, pp. 422–424 (1974), "Androgen receptors in a Syrian hamster ductus deferens tumour cell line".

Hori et al., J. of Antibiotics, vol. 46, No. 9, pp. 1327–1333 (1993), "WB2838 [3–chloro–4–(2–amino–3–chlorophenyl)–pyrrole]: non–steroidal androgen–receptor antagonist produced by a Pseudomonas".

Wong, "Synthesis and some related studies of alkyl 2,3–bis-(alkylidene)–cyclopentanecarboxylates", Ph.D. thesis, University of British Columbia, Dec., 1993.

Rasmusson et al., Ann. Rep. Med. Chem., vol. 29 (1994), pp. 225–234, "Therapeutic control of androgen action".

Tilley et al., Proc. Nat'l Acad. Sci. USA, vol. 86 (1989), pp. 327–331, "Characterization and expresion of a cDNA encoding the human androgen receptor".

Summerfield et al., Mol. Pharm., vol. 47 (1995), pp. 1080–1088, "Tissue–specific pharmacology of testosterone and 5alpha–dihydrotestosterone analogues . . . ".

Syms et al., J. Steroid Biochem., vol. 28 (1987), pp. 109–116, "Glucocorticoid effects on growth, and androgen receptor concentrations in DDT1MF–2 cell lines".

Harris et al., Molecular Endocrinology, vol. 3 (1989), pp. 1839–1844, "Androgens and glucocorticoids modulate heparin–binding growth factor 1 mRNA accumulation in DDT1 cells as analyzed by in situ hybridization".

Smith et al., J. Steroid Biochem., "Differential Effects of Androgens and Glucocorticoids on Regulation . . . ", vol. 20, No. 1, pp. 277–281 (1984).

Smith et al., J. Steroid Biochem., "Steroid Regulation of Receptor Concentration and Oncogene Expression", vol. 24, No. 1, pp. 51–55 (1986).

Neri et al., Anticancer Research, "Complete Androgen Blockade as Treatment for Advanced Prostate Cancer . . . ", vol. 9, pp. 13–16 (1989).

Turcotte et al., J. Steroid Biochem, "Androgen Binding as Evidence by a Whole Cell Assay System . . . ", vol. 29, No. 1, pp. 69–76 (1988).

Toney et al., J. Steroid Biochem. Molec. Biol., "Non–steroidal L–245,976 Acts as a Classical Antiandrogen In Vivo", vol. 60, No. 1–2, pp. 131–136, 1997.

Primary Examiner—David M. Naff
Assistant Examiner—Janet M. Kerr
Attorney, Agent, or Firm—Catherine D. Fitch; Melvin Winokur

[57] ABSTRACT

An assay for identifying compounds with antiandrogenic activity employing a hamster ductus deferens cell line (DDT1) ATCC CRL-1701 and ATCC CRL-12051 is disclosed, as well as antiandrogenic compounds identified from this assay, particularly the nonsteroidal compound N-(4-chlorophenyl)-(Z,Z)-2,3-bis(cyclopropylmethylene) cyclopentane carboxamide of structural formula (I):

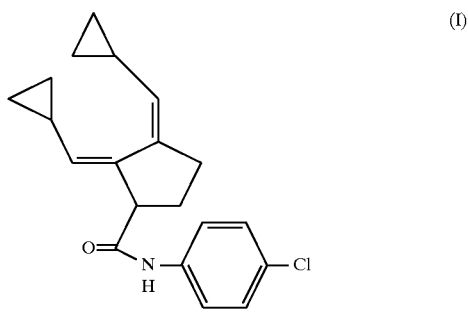

This compound is an antiandrogen useful in the treatment and prevention of diseases of the prostate including prostatitis, benign prostatic hyperplasia (BPH) and prostatic carcinoma.

4 Claims, 2 Drawing Sheets

TREATMENT OF PROSTATE DISEASE WITH A NONSTEROIDAL ANTI-ANDROGENIC COMPOUND

CROSS REFERENCE TO RELATED APPLICATIONS

The present application claims priority of provisional application 60/012,638, filed Mar. 1, 1996.

SUMMARY OF THE INVENTION

The present invention relates generally to a novel assay for identifying compounds with antiandrogenic activity as well as to antiandrogenic compounds identified from this assay. The assay employs a hamster ductus deferens cell line (DDT1) ATCC CRL-1701 and ATCC CRL-12051 that is highly dependent on the addition of testosterone in synthetic serum-free media.

The nonsteroidal compound N-(4-chlorophenyl)-(Z,Z)-2,3-bis(cyclopropylmethylene)cyclopentane carboxamide of structural formula (I):

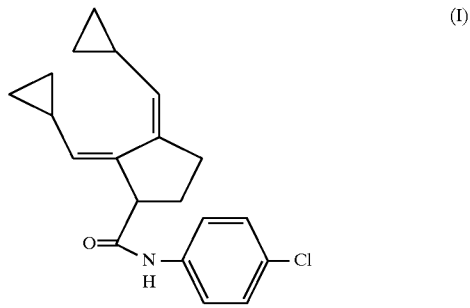

(I)

has been identified using the assay of the present invention as an antiandrogenic compound useful in the treatment and prevention of diseases of the prostate including prostatitis, benign prostatic hyperplasia (BPH) and prostatic carcinoma.

The present invention also provides for novel compositions employing compounds which exhibit antiandrogenic activity in the assay of the present invention. The compounds which exhibit antiandrogenic activity in the assay of the present invention are useful in the systemic, including oral, and parenteral, including topical, treatment and prevention of diseases of the prostate including prostatic carcinoma, benign prostatic hyperplasia and prostatitis.

The compounds, including N-(4-chlorophenyl)-(Z,Z)-2,3-bis(cyclopropylmethylene)cyclopentane carboxamide, identified as androgen antagonists in the assay of the present invention may be used in combination with other active agents, for example, a 5α-reductase inhibitor such as finasteride, epristeride, 17β-N-(2,5-bis(trifluoromethyl))phenylcarbamoyl-4-aza-5α-androst-1-en-3-one, or the compounds described in PCT publication WO 95/11254, or an α1- or α1$_a$-andrenergic receptor antagonist, or combinations of such other active agents with the androgen antagonist compound identified from the present assay, wherein such combinations would be useful in one or more of the above-mentioned methods of treatment or pharmaceutical compositions.

BACKGROUND OF THE INVENTION

The DDT1 cell line has been reported to be an androgen-responsive cell line. Norris et al. "Androgen Receptors in a Syrian Hamster Ductus Deferens Tumour Cell Line," Nature 248:422–424 (1974). Syms et al., "Glucocorticoid Effects on Growth, and Androgen Receptor Concentrations on DDT$_1$MF-2 Cell Lines", J. Steroid Biochem., 28(2):109–116 (1987) report that the DDT$_1$-MF-2 smooth muscle tumor cell line contains receptors for and is differentially sensitive to androgens and glucocorticoids. They report that androgens stimulate growth, and glucocorticoids inhibit growth of the cell line.

Harris et al., "Androgens and Glucocorticoids Modulate Heparin-Binding Growth Factor I mRNA Accumulation in DDT1 Cells as Analyzed by in situ Hybridization", Mol. Endo. 3(11):1839–1844 (1989), describe the ductus deferens smooth muscle tumor cell line (DDT$_1$-MF-2) as steroid-sensitive. They report that treatment with 10 nM testosterone accelerated the growth of DDT1 cells in the absence of serum, and that glucocorticoids inhibit growth. They further identify the DDT$_1$-MF-2 cell line as a useful model for steroid responsive tumor growth in vitro.

There has been a need for tissue culture models that mimic the androgen responsiveness observed in androgen sensitive diseases, particularly that observed in human prostatic carcinomas. The present invention provides for an assay to study compounds as potential anti-androgens in living cells.

Lippman et al. in "The Effects of Androgens and Antiandrogens on Hormone-response Human Breast Cancer in Long-Term Tissue Culture" Cancer Research 30: 4610–4618 (1976), describe the MCF-7 androgen-responsive cell line. Unlike the cell line of the present invention, the MCF-7 cell line cannot be grown in synthetic media.

Similarly, Marugo et al. in "Effects of Dihydrotestosterone and Hydroxyflutamide on Androgen Receptors in Cultured Human Breast Cancer Cells (EVSA-T)" J. Steroid Biochem. Mole. Biol. 42(5):547–554 (1992), describe another androgen responsive cell line. However, like the cells of the MCF-7 cell line, these cells cannot be grown in synthetic media.

The human androgen receptor has been isolated and characterized.

Tilley et al., "Characterization and Expression of a cDNA Encoding the Human Androgen Receptor", Proc. Nat'l. Acad. Sci. USA, 80:327–331 (1989) report the isolation, characterization and expression of the cDNA encoding the human androgen receptor, which predicts a protein of 917 amino acids and a molecular weight of 98918.

Rasmusson et al., "Therapeutic Control of Androgen Action", Ann. Rep. Med. Chem. 29:225–234 (1994) present a review of the androgen receptor, chemical antagonists of the androgen receptor, and means of controlling androgen biosynthesis.

Compounds identified as anti-androgens by the assay of the present invention are especially useful in the prevention and treatment of prostatic carcinoma, and they may also be useful in the treatment and prevention of other hyperandrogenic diseases such as acne vulgaris, seborrhea, female hirsutism, androgenetic alopecia, also called androgenic alopecia, which includes male and female pattern baldness, and benign prostatic hyperplasia.

Benign prostatic hyperplasia (BPH) and prostatic carcinoma are among the most common afflictions of aging men.

Benign prostatic hyperplasia is often treated surgically with a procedure known as transurethral resection of the prostate (TURP). Other surgical procedures performed to release the obstruction of urine include incision or stents. Castration has also resulted in regression of prostatic enlargement. Drug therapy for BPH has included alpha-1 blockers which treat the symptoms of the disease by alleviating obstructive symptoms, but do not affect the underlying cause of the disease, the enlarged prostate gland. Representative alpha-1 blockers used in the treatment of BPH include: prazosin, terazosin, doxazosin, tamsulosin and alfuzosin. These drugs relax prostatic smooth muscle tone, decreasing intraurethral pressure without affecting bladder pressure. Common side effects of these agents are dizziness, headache and fatigue.

Finasteride (17β-(N-tert-butylcarbamoyl)-4-aza-5α-androst-1-ene-3-one), which is marketed by Merck & Co., Inc., under the tradename PRQSCAR®, is an inhibitor of testosterone 5α-reductase currently marketed for the treatment of benign prostatic hyperplasia. A principal mediator of androgenic activity in the prostate is 5α-dihydrotestosterone ("DHT"), formed locally in the prostate by the action of testosterone-5α-reductase. Inhibitors of testosterone-5α-reductase inhibit the conversion of testosterone (T) to DHT and serve to prevent or lessen symptoms of hyperandrogenic stimulation in the prostate. See especially U.S. Pat. No. 4,377,584 assigned to Merck & Co., Inc., issued Mar. 22, 1983. The utility of finasteride in the treatment of prostatic carcinoma is also disclosed in the following documents: EP 0 285,382, published 5 Oct. 1988; EP 0 285 383, published 5 Oct. 1988; Canadian Patent no. 1,302,277; and Canadian Patent no. 1,302,276.

Both prostatic carcinoma and BPH have been treated with antiandrogens. Nonsteroidal antiandrogens such as flutamide and Casodex compete with DHT for androgen receptor sites in the prostate cells. These non-steroidal antiandrogens do not substantially change sexual potency and libido as the gonadotrophin releasing hormone agonists and progestogens do; however, these nonsteroidal antiandrogens often exhibit the undesirable tendency to feminize the male host (gynaecomastia) or initiate feed-back effects which would cause hyperstimulation of the testes.

Gonadotrophin-releasing hormone (GnRH) agonists such as nafarelin, buserelin, goserelin and leuprorelin all reduce the release of leutinizing hormone (LH) by desensitizing the GnRH receptors in the anterior pituitary gland. GnRH agonists are able to reduce the production of testosterone, induce shrinkage of prostate volume and reduce the severity of urinary symptoms of BPH. Unfortunately, these drugs have adverse effects such as impotence and flushing, which discourage a majority of patients from continuing with the drugs. These androgen-suppressing agents are thus of inconsequential significance in BPH treatment, but are of major importance in the treatment of patients with advanced prostatic cancer.

Progestogens, such as megestrol acetate, hydroxyprogesterone and medrogestone depress testosterone by inhibiting LH release and blocking androgen receptors, causing a reduction in prostatic volume. Adverse effects such as decreased libido and impotence have kept progestogens from common use in BPH treatment.

Thus, there still remains a need for additional therapies for BPH and prostatic carcinoma for individuals who cannot tolerate the side effects and/or do not experience adequate relief from presently available therapies.

There also remains a need for a compound for the treatment of diseases of the prostate that is a non-steroidal compound having different pharmacological properties from steroids.

Hori et al. "WB2838 [3-Chloro-4-(2-amino-3-chlorophenyl)-pyrrole]: Non-steroidal androgen-receptor antagonist produced by A Pseduomonas" J. Antibiotics 46(9):1327–1333 (1993) describe the nonsteroidal androgen receptor antagonist labeled WB2838:

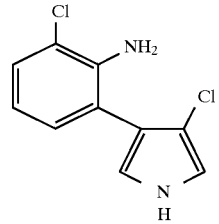

WB2838

N-(4-chlorophenyl)-(Z,Z)-2,3-bis(cyclopropylmethylene) cyclopentane carboxamide is described by T. Wong "Synthesis nad Some Related Studies of Alkyl 2,3-bis (alkylidene)cyclopentance carboxylates", Ph.D. thesis, University of British Columbia, December, 1993. No use for this compound is described in the thesis.

Steroid hormones are involved in numerous aspects of cell growth and differentiation. In an effort to influence these processes chemists have developed analogs usually based on the four ring steroid nucleus. Nonsteroidal compounds interacting with steroid receptors are more rare and exhibit different pharmacological properties from their steroidal counterparts. We describe the use of androgen receptor binding assays and androgen-dependent DDT1 cells to identify and characterize novel antiandrogens, of particular interest are nonsteroidal antiandrogens.

DETAILED DESCRIPTION OF THE INVENTION

Figure 1:
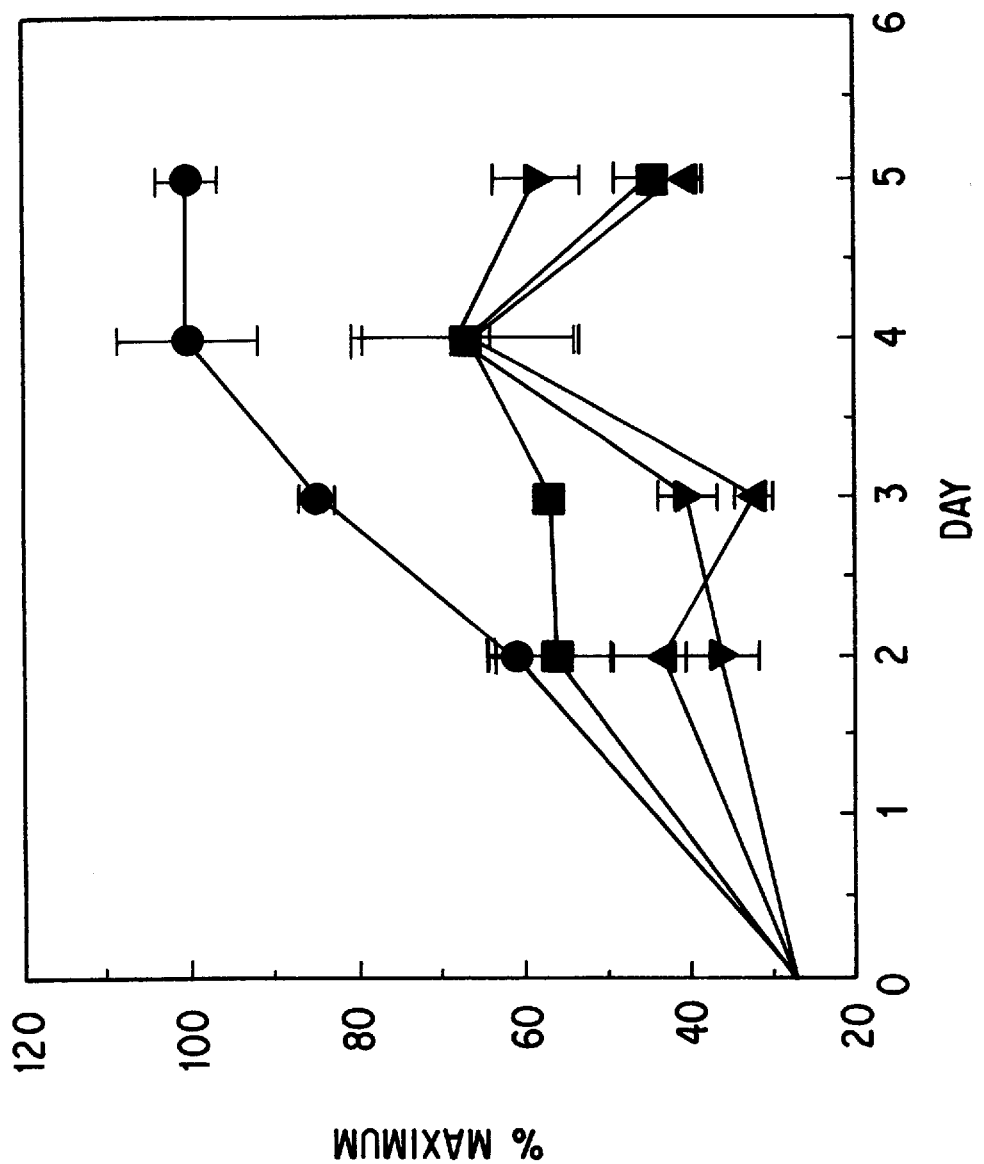
FIG. 1 is a graph of the results of two independent runs of the experiment described in Example 1. This graph shows the androgen dependent growth of DDT1 cells. Cells were plated in a 96 well plate at 2,000 cells/well in DFITS+0.1% fetal calf serum. After 24 hours, the cells were washed with the same medium except without added serum and replaced with fresh serum free DFITS (day 0) with ethanol mock control (open squares), with 10 nM testosterone (open circles), with 10 μM N-(4-chlorophenyl)-(Z,Z)-2,3-bis (cyclopropylmethylene)cyclopentane carboxamide alone (filled squares), or 10 μM N-(4-chlorophenyl)-(Z,Z)-2,3-bis (cyclopropyl-methylene)cyclopentane carboxamide in the presence of 10 nM testosterone (filled circles). Cell growth data were normalized to the greatest number of cells and error bars represent +/- one standard error of the mean (sem).

The present invention relates to a method for determining the antiandrogenic action of a compound comprising:

(a) plating DDT1 cells (ATCC CRL-12051) in medium free from androgens;

(b) adding a solution containing the compound to the plated DDT1 cells;

(c) measuring the growth of the DDT1 cells in the presence of the compound over a measured period of time.

In one embodiment of the present invention, the method for determining the antiandrogenic action of a compound comprises:

(a) plating DDT1 cells (ATCC CRL-12051) in medium free from androgens;

(b) adding a solution containing the compound to the plated DDT1 cells;

(c) measuring the growth of the DDT1 cells in the presence of the compound over a measured period of time and calculating a rate of growth of the DDT1 cells.

In one aspect of the present invention, the DDT1 cells are grown in synthetic serum-free media. The DDT1 cell line, also referred to as the DDT1 MF-2 cell line, was an existing deposit with the American Type Culture Collection ATCC No. CCRL-1701 which has been re-deposited with the American Type Culture Collection (ATCC), 12301 Parklawn Drive, Rockville, Md. United States of America under the conditions of the Budapest Treaty as ATCC CRL-12051 on Feb. 21, 1996. The DDT1 smooth muscle cell line was cloned from cells derived from a leiomyosarcoma of the ductus deferens of a Syrian hamster (*Mesocricetus auratus*). It has maintained androgen and glucocorticoid receptors and alpha 1 and beta 2 adrenergic receptors. The beta 2 adrenergic receptor is functionally coupled to adenylate cyclase. Glucocorticoids regulate the expression of the c-sis proto-oncogene (inhibit). Growth is stimulated by androgens and inhibited by glucocorticoids.

Preferably, the method of the present invention is carried out by comparing the rate of growth of DDT1 cells in the presence of the compound to the rate of growth of DDT1 cells in the absence of the compound. In one embodiment of the present invention, a known volume of the solution containing the compound is added to the plated DDT1 cells. In a further illustration of the present invention, the solution of the compound is of a known concentration. When a known volume of a known concentration of the compound is added and the resulting rate of growth of the DDT1 cells is compared to the rate of growth when a "blank" solution is added (a volume of the solvent used to dissolve the compound equal to the volume of the solution containing the compound in the comparative run), the $IC_{50}$ of the compound may be computed. The compound may be dissolved in a suitable solvent such as DMSO, ethanol, water or methylethyl ketone (MEK)> Preferably, the compound is dissolved in ethanol to form an ethanol solution. In one aspect of the present invention, a known volume of a known concentration of the ethanol solution is added. In a further aspect of the present invention, the rate of growth of the DDT1 cells when a known volume of a known concentration of the compound in an ethanol solution cells is compared to the rate of growth of DDT1 cells when the same volume of ethanol is added.

In one embodiment of the present invention, the growth of the DDT1 cells is measured over the period of one hour.

In one class of the present invention, the measurement of the growth of the DDT1 cells over the measured period of time is performed by counting the number of cells at the beginning and at the end of the period of time. This can be done by quantitating cells using a hemocytometer.

In another class of the present invention, the measurement of the growth of the DDT1 cells over the measured period of time is performed by incubating the DDT1 cells with labeled thymidine and measuring the incorporation of the label as a measure of DNA synthesis. Preferably, the labeled thymidine is $^3$H-thymidine, and the incorporation of the tritium label is measured by incubating cells for a period of time, preferably overnight, and washing extensively to remove free $^3$H-thymidine. Cells are then removed, preferably using trypsin, resuspended in media and the radioactivity quantitated, preferably by scintillation counting, for example using a Tri-Carb 2500TR Liquid Scintillation analyzer manufactured by Packard.

In still another class of the present invention, the measurement of the growth of DDT1 cells is measured by colorimetric analysis. In particular, the growth may be measured by diluting 3-(4,5-dimethyl-thiazol-2-yl)-5-(3-carboxylmethoxy phenyl)-2-(4-sulfophenyl)-2H-tetrazolium into the medium and adding phenazine methosulfate, and measuring the absorbance at 490 nm.

In one embodiment of the present invention, the cells are plated in 96 well plates. In a preferred class of this embodiment of the invention, the assay is automated; i.e., the solutions are dispensed using a robotic device.

In one embodiment of the method of the present invention, the tested compound is assayed to determine that the compound inhibits the binding of labeled dihydrotestosterone (DHT) to the androgen receptor (AR). The androgen receptor used in the assay can be obtained from tissue such as prostate or liver, preferably human tissue, or cloned from the known sequence, see Tilley et al., Proc. Nat'l. Acad. Sci. USA, 80:327–331 (1989). Alternatively, the source of the human androgen receptor can be a cell line transfected with the human androgen receptor. Techniques for obtaining these transfected cell lines are well-known in the art and are preferred because of the uniformity of the receptor produced. The androgen receptor is incubated with labeled DHT, particularly $^3$H-DHT, and the compound to be tested or unlabelled DHT is added to the incubated receptor. The unlabelled DHT may be run in a parallel experiment in order to quantitate the nonspecific binding. The affinity for the androgen receptor is then calculated. One method of calculating this affinity is to add an agent to remove free labeled DHT. This may be done by a charcoal technique by adding dextran-coated charcoal to the sample at 0.5 volume of the original assay volume, vortexing, and centrifuging at 3,000×g for 15 minutes at 4° C. Bound labeled DHT (preferably $^3$H-DHT) is in the supernatant. In a filter binding assay, the bound androgen receptor-labeled DHT (preferably AR-$^3$H-DHT) complexes can be precipitated using agents such as ammonium sulfate, and filtered through glass fiber membranes. After extensive washing, bound labeled DHT (preferably $^3$H-DHT) is measured. When $^3$H-DHT is employed, the remaining label may be measured by scintillation counting of the glass fiber membranes, for example using a Tri-Carb 2500TR Liquid Scintillation analyzer manufactured by Packard. The compound may be tested for its ability to inhibit binding of DHT to the androgen receptor either before or after determining the antiandrogenic action of the compound according to the method of the present invention.

The present invention presents a convenient assay for monitoring the effect of compounds in a tissue culture system and demonstrates that the result of such an assay is the discovery of a nonsteroidal compound that acts as an antiandrogen.

Further, the present invention relates to a method of treating or preventing diseases of the prostate comprising administering 0.001 to 200 mg per day of a compound capable of inhibiting androgen-induced DDT1 cell growth to a male human in need of such treatment.

The instant invention involves a method of treating and/or preventing BPH and prostatic carcinoma which comprises administering to a patient in need of such treatment a therapeutically effective amount of a compound which inhibits the testosterone induced growth of DDT1 cells. In one embodiment of this method, the compound which inhibits the testosterone-induced growth of DDT1 cells is administered in a dosage amount between 0.001 to 200.0 mg/day. In one class of this embodiment, the compound which inhibits the testosterone-induced growth of DDT1 cells is administered in a dosage amount of from 0.01 to 50.0 mg/day, and in a sub-class of this embodiment, the compound which inhibits the testosterone-induced growth of DDT1 cells is administered in a dosage amount of about 0.1 to 5.0 mg/day. Compounds which inhibit the testosterone-induced growth of DDT1 cells can be determined by employing the assay described in Example 1.

In a second embodiment of this invention, the methods of treating and preventing benign prostatic hyperplasia and prostatic carcinoma comprise administration to a patient in need of such treatment of a compound which inhibits the testosterone-induced growth of DDT1 cells. Preferably, this compound is a non-steroidal compound.

Preferred compounds that may be employed in the present invention include N-(4-chlorophenyl)-(Z,Z)-2,3-bis (cyclopropylmethylene)cyclopentane carboxamide of structural formula (I):

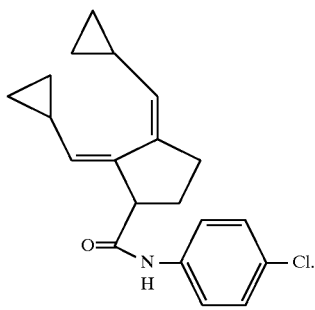

(I)

and pharmaceutically acceptable salts, esters and prodrugs thereof.

The nonsteroidal compound N-(4-chlorophenyl)-(Z,Z)-2, 3-bis(cyclopropylmethylene)cyclopentane carboxamide which antagonizes the action of testosterone on DDT1 cells but exhibits little or no effect on cell growth by itself. This compound also blocks the binding of $^3$H-DHT to the human androgen receptor expressed in stable transfectants of CHO cells at doses comparable to those that antagonize testosterone in DDT1 cells. This compound may thus represent a novel class of nonsteroidal antiandrogens which show promise in the treatment of prostate cancer.

The present invention has the objective of providing methods of treating and preventing diseases of the prostate including BPH and prostatic carcinoma by systemic, oral, parenteral or topical administration of a compound which inhibits the testosterone-induced growth of DDT1 cells in a dosage amount between 0.001 to 200.0 mg/day, and more particularly, from about 0.01 to 50.0 mg/day, and most particularly 0.1 to 5.0 mg/day. The term "treating BPH" is intended to include alleviating the obstructive symptoms of BPH, and slowing and/or reversing the growth of the prostate. The term "preventing BPH" is intended to include preventing development of obstructive symptoms, and preventing the enlargement of the prostate. The term "treating prostatic carcinoma" is intended to include slowing and/or stopping the growth of prostatic carcinoma. The term "preventing prostatic carcinoma" is intended to include preventing the development of prostatic carcinoma in patients likely to develop prostatic carcinoma. Also, a compound which inhibits the testosterone-induced growth of DDT1 cells may be co-administered with a 5α-reductase 2 inhibitor, such as finasteride or epristeride; a 5α-reductase 1 inhibitor such as 4,7β-dimethyl-4-aza-5α-cholestan-3-one, 3-oxo-4-aza-4, 7β-dimethyl-16β-(4-chlorophenoxy)-5α-androstane, and 3-oxo-4-aza-4,7β-dimethyl-16β-(phenoxy)-5α-androstane as disclosed in WO 93/23420 and WO 95/11254; dual inhibitors of 5α-reductase 1 and 5α-reductase 2 such as 3-oxo-4-aza-17β-(2,5-trifluoromethylphenylcarbamoyl)-5α-androstane as disclosed in WO 95/07927; nonsteroidal antiandrogens such as flutamide and Casodex, and alpha-1 blockers such as prazosin, terazosin, doxazosin, tamsulosin, and alfuzosin. The term "co-administered" includes concurrent administration as well as separate provision of the identified medicaments.

The present invention also has the objective of providing suitable systemic, oral, parenteral and topical pharmaceutical formulations for use in the novel methods of treatment of the present invention. The compositions containing as an active ingredient a compound which inhibits the testosterone-induced growth of DDT1 cells can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions. Likewise, they may also be administered in intravenous (both bolus and infusion), intraperitoneal, subcutaneous, topical with or without occlusion, or intramuscular form, all using forms well known to those of ordinary skill in the pharmaceutical arts. For oral administration, for example, the compositions can be provided in the form of tablets containing 0.01, 0.05, 0.1, 0.2, 1.0, 2.0, 5.0, 10.0, 50.0 and 100.0 milligrams of the active ingredient for the adjustment of the dosage to the patient to be treated.

The compound which inhibits the testosterone-induced growth of DDT1 cells may be administered in a pharmaceutical composition comprising the active compound in combination with a pharmaceutically acceptable carrier adapted for topical administration. Topical pharmaceutical compositions may be, e.g., in the form of a solution, cream, ointment, gel, lotion, shampoo or aerosol formulation adapted for application to the skin. Topical pharmaceutical compositions useful in the method of treatment of the present invention may include about 0.001% to 0.1% of the active compound in admixture with a pharmaceutically acceptable carrier.

Advantageously, compounds of the present invention may be administered in a single daily dose, or the total daily dosage may be administered in divided doses of two, three or four times daily. The compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of the drug.

In the methods of the present invention, the compound which inhibits the testosterone-induced growth of DDT1 cells herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Capsules containing the product of this invention can be prepared by mixing an active compound of the present invention with lactose and magnesium stearate, calcium stearate, starch, talc, or other carriers, and placing the mixture in a gelatin capsule. Tablets may be prepared by mixing the active ingredient with conventional tableting ingredients such as calcium phosphate, lactose, corn starch or magnesium stearate. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may be administered in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations. See, e.g., EP 0 285 382.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Thus, the present invention also provides for a pharmaceutical composition for the treatment of diseases of the prostate comprising a compound capable of inhibiting androgen induced DDT1 cell growth and a pharmaceutically acceptable carrier. In one class of this embodiment of the invention, the compound capable of inhibiting androgen-induced DDT1 cell growth is N-(4-chlorophenyl)-(Z,Z)-2,3-bis(cyclopropylmethylene)cyclopentane carboxamide of structural formula (I):

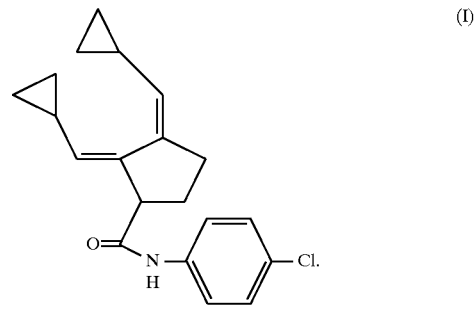

The present invention also provides for the use of a compound which inhibits the testosterone-induced growth of DDT1 cells in the preparation of a medicament useful in the treatment of diseases of the prostate.

The following examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds.

All temperatures given in the following examples are in degrees Celsius.

EXAMPLE 1

DDT1 Assay

DDT1 cells (ATCC Nos. CRL-1701 and CRL-12051) were maintained in Dulbecco's modified Eagle's medium (GIBCO BRL) (DMEM)+2% bovine calf serum (Hyclone®, BCS defined, iron supplemented) and 10 nM testosterone. Media was charged every 48 hours. Cells were plated at ~2,000/well in 96-well plates or ~6,000 cells/cm$^2$ in DMEM: F12 (GIBCO BRL) nutrient mixture (1:)+ITS™ (insulin, transferrin, selenious acid) (Collaborative Biomedical Products/Becton Dickinson Labware) (final concentrations 5 µg/mL insulin, 5 µ/mL transferrin, 5 ng/mL selenious acid) (DFITS media)+0.1% bovine calf serum (Hyclon®, BCS defined, iron supplemented).

After 24 hours, the cells were washed with the same media except without added serum and replaced with fresh serum-free DFITS medium (day 0).

In a typical experiment, cells were plated in sets of 12 in the presence of either a mock ethanol control (0.1–0.2% total volume) or N-(4-chlorophenyl)-(Z,Z)-2,3-bis (cyclopropylmethylene) cyclopentane carboxamide dissolved in 100% ethanol as a 1000X concentrated stock solution. Cell growth was then measured using a CellTiter96™ Non-Radioactive Cell Proliferation Assay (Promega Corporation) according to the manufacturer's protocol using a Bio Kinetics EL 340 microplate reader (BioTek Instruments, Inc.). 3-(4,5-dimethylthiazol-2-yl)-5-(3-carboxyl methoxyphenyl)-2-(4-sulfophenyl)-2H-tetrazolium (MTS) was diluted into media at a final concentration of 333 μg/mL and penazine methosulfate (PMS) was used at a final concentration of 25 μM with a total volume per well of 100 μL. Plates were then incubated for one hour at 37° C. in a humidified 5% $CO_2$ atmosphere. A linear response between cell number and absorbance at 490 nm was found up to 20,000 cells/well. The proliferation of DDT1 cells in synthetic serum-free medium is very slow doubling time >5 days in the absence of added testosterone, but is robust in the presence of 10 nM testosterone as shown in FIG. 1. The addition of either N-(4-chlorophenyl)-(Z,Z)-2,3-bis(cyclopropylmethylene)cyclopentane carboxamide or an ethanol mock control showed little or no effect on cell proliferation. In contrast, the addition of N-(4-chlorophenyl)-(Z,Z)-2,3-bis(cyclopropylmethylene)cyclopentane carboxamide at 10 μM along with 10 nM testosterone reduced cell proliferation to levels close to that of the ethanol mock control. The classical nonsteroidal antiandrogen flutamide at 1 μM had the same effect, within experimental error, of blocking testosterone in this system. Thus N-(4-chlorophenyl)-(Z,Z)-2,3-bis(cyclopropylmethylene) cyclopentane carboxamide inhibits testosterone-induced DDT1 cell growth in a manner similar to that of hydroxyflutamide.

EXAMPLE 2
Binding to the Androgen Receptor

100 μL of cytosol (100,000×g supernatant) were incubated overnight at 4° C. in the presence of 1 nM [$^3$H]-DHT with and without unlabelled DHT at 1 μM to assess non-specific binding with and without added compound to measure competition. All samples were prepared in duplicate. Compound stock solutions were typically 100 fold concentrated in 100% ethanol and equal volumes of ethanol were employed as a mock control. Free steroids were removed by addition of dextran-coated charcoal followed by centrifugation at 3,000×g for fifteen minutes at 4° C. Receptor-bound [$^3$H]-DHT was then measured by Scintillation counting of the supernatants.

Binding to the human androgen receptor (hAR) was measured essentially as described by Tilley et al., "Characterization and expression of cDNA encoding the human androgen receptor", Proc. Nat'l Acad. Sci. USA 86:327–331 (1989), and Summerfield et al., "Tissue-specific pharmacology of testosterone and 5α-dihydrotestosterone analogues: characterization of a novel canine androgen-binding protein", Mol. Pharm. 47: 1080–1088 (1995) except that stable transfectants of CHO cells were employed (gift from Prof. Michael McPhaul Southwestern Medical Center, Dallas, Tex.) that typically express 30–80 fmoles receptor/mg soluble protein.

N-(4-chlorophenyl)-(Z,Z)-2,3-bis(cyclopropylmethylene) cyclopentane carboxamide exhibits an $IC_{50}$ (fifty percent displacement ($IC_{50}$) of 3H-5α-DHT (1.0 nM) of 27.5±0.13 μM (two independent experiments). Hydroxyflutamide has an $IC_{50}$~100 nM using the same binding assay.

EXAMPLE 3
Preparation of N-(4-chlorophenyl-(Z,Z)-2,3-bis(cyclopropylmethylene)cyclopentanecarboxamide To a stirred solution of 4-chloroaniline (66 mg, 0.52 mmol) in dry benzene (2.6 mL, argon atmosphere) was added a solution of trimethylaluminum in toluene (0.26 mL, 2M, 0.52 mmol) and the mixture was stirred at room temperature for 20 minutes. A solution of methyl (Z,Z)-2,3-bis(cyclopropylmethylene)cyclopentanecarboxylate (80 mg, 0.344 mmol) in dry benzene (2.0 mL) was added and the mixture was refluxed for 4 hours. Hydrochloric acid (2M, 4 mL) was added and the phases were separated. The aqueous phase was extracted three times with diethyl ether. The combined organic extracts were washed (brine), dried (magnesium sulfate) and concentrated. Flash chromatography (20 g silica gel, 4:1 petroleum ether-diethyl ether) of the crude product and removal of traces of solvent (vacuum pump) from the acquired material produced 93.5 mg (83%) of the amide, N-(4-chlorophenyl)-(Z,Z)-2,3-bis (cyclopropylmethylene)cyclopentane carboxamide. Recrystallization of this material from 1:1 dichloromethane-ethanol gave the amide N-(4-chlorophenyl)-(Z,Z)-2,3-bis (cyclopropylmethylene)cyclopentane carboxamide as colorless needle-like crystals (mp 126°–127° C.) that showed IR (KBr): 3255, 1664, 1594, 1494, 1399, 1096, 824 $cm^{-1}$; $^1$H NMR ($CDCl_3$, 400 MHz): 0.42–0.60 (m, 4H), 0.80–0.95 (m, 4H), 1.77–1.90 (m, 2H), 2.00–2.10 (m, 1H), 2.10–2.22 (m, 1H), 2.35–2.53 (m, 2H), 3.40 (dd, 1H, J=9, 4 Hz), 4.87 (d, 1H, J=10 Hz), 4.96 (d, 1H, J=10 Hz), 7.26 (d, 2H, J=9 Hz), 7.44 (d, 2H, J=9 Hz), 7.56 (br s, 1H, $w_{1/2}$=8 Hz); in a decoupling experiment, irradiation at δ 1.82 simplified the multiplets at 0.42–0.60 and 0.80–0.95, and simplified the two doublets at 4.87 and 4.96 to two broad singlets ($w_{1/2}$=5, 3 Hz, respectively); in a series of NOE difference experiments, irradiation at δ 3.40 caused enhancement of the signals at 2.10–2.22 (9%) and 4.96 (10%); irradiation at δ 4.87 caused enhancement of the signals at 1.77–1.90 (4%) and 2.35–2.53 (3%); irradiation at δ 4.96 caused an enhancement of the signal at 3.40 (4%); $^{13}$C NMR ($CDCl_3$, 50.3 MHz): δ 6.9, 7.1, 8.5, 8.9, 13.8, 14.1, 26.9, 31.9, 53.3, 120.6, 128.85, 128.9, 130.2, 133.6, 135.6, 136.2, 136.8, 173.3. Exact mass calcd. for $C_{20}H_{22}{}^{35}ClNO$: 327.1392; found: 327.1384. Anal. calcd. for $C_{20}H_{22}ClNO$: C 73.27, H 6.76, N, 4.27; found: C 73.17, H 6.67, N, 4.40.

EXAMPLE 4

Ligand dependent transcription assays were performed as described in Schnmidt et al. "Identification of a new member of the steroid hormone receptor superfamily that is activated by a peroxisome proliferator and fatty acids," Mol. Endocrinol. 6:1634–1641 (1992). A luciferase cDNA expressed under the control of the promoter region of the probasin gene that confers androgen receptor dependent transcription was used as a reporter gene, see Rennie et al. "Characterization of two cis-acting DNA elements involved in the androgen regulation of the probasin gene" Mol Endocrinol. 7:23–36 (1993). The promoter region, −426 to +40 of the rat probasin gene was amplified by polymerase chain reaction (PCR) and inserted upstream of the luciferase cDNA of pGL3 Basic plasmid (Promega). The expression vector pSGAR that expressed the normal human AR was used as a source of receptor, see, Chang et al. "Molecular cloning of human and rat complementary DNA encoding androgen receptors," Science 240:324–326 (1988). Transient transfection of CV1 cells was performed by plating cells (1.5×$10^5$ per mL) into 12 well dishes in phenol red-free medium supplemented with 10% fetal calf serum treated with activated charcoal to remove endogenous steroids. Cells were then transfected the following day by addition of a calcium phosphate precipitate of plasmid DNA. Cells were then washed with fresh media after an overnight incubation and ligands were added. Cell extracts were prepared after forty eight hours and assayed for luciferase enzyme activity using the Luciferase Assay System (Promega). Each transfection was performed in triplicate and the fluorescence of each sample was measured using the AutoChemiluminometer (Berthold).

Figure 2:
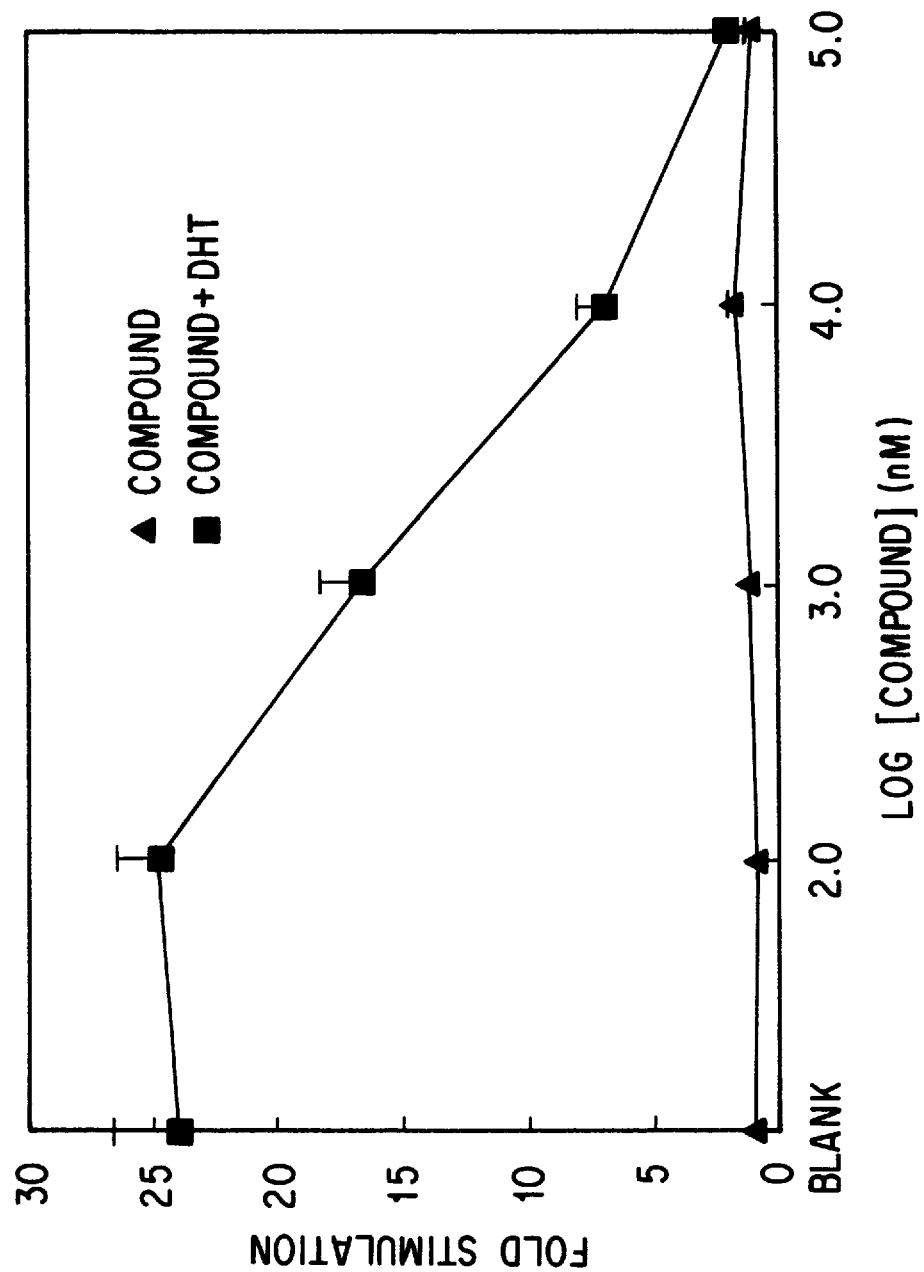
FIG. 2 is a graph showing the effect of N-(4-chlorophenyl)-(Z,Z)-2,3-bis(cyclopropyl-methylene) cyclopentane carboxamide on the activation of the androgen receptor in CV1 cells, as described in Example 4. The filled triangles represent N-(4-chlorophenyl)-(Z,Z)-2,3-bis (cyclopropylmethylene)cyclopentane carboxamide alone, the filled squares represent N-(4-chlorophenyl)-(Z,Z)-2,3-bis(cyclopropylmethylene)cyclopentane carboxamide plus 10 nM dihydrotestosterone (DHT).

Thus to test whether N-(4-chlorophenyl-(Z,Z)-2,3-bis (cyclopropyl-methylene)cyclopentanecarboxamide acts as an agonist or antagonist to the androgen receptor, the effect of N-(4-chlorophenyl-(Z,Z)-2,3-bis(cyclopropyl-methylene)cyclopentanecarboxamide on either the AR dependent transcription from the pPBluc reporter gene or the ability of N-(4-chlorophenyl-(Z,Z)-2,3-bis (cyclopropylmethylene) cyclopentanecarboxamide to block the androgen receptor transactivation by DHT. The androgen receptor and the probasin luciferase reporter gene were co-transfected into CV1 cells and N-(4-chlorophenyl-(Z,Z) -2,3-bis(cyclopropyl-methylene)cyclopentane carboxamide was added to the cells without or with 10 nM DHT. Treatment using N-(4-chlorophenyl-(Z,Z)-2,3-bis (cyclopropylmethylene)cyclopentane carboxamide alone did not affect luciferase expression from the pPBluc reporter gene. In contrast, N-(4-chlorophenyl-(Z,Z)-2,3-bis (cyclopropylmethylene)cyclopentane carboxamide inhibited the transactivation mediated by DHT in a dose dependent manner. Fifty percent inhibition of transactivation occurred at about 2 µM and maximal inhibition occurred at 100 µM. The results are graphed in FIG. 2.

TABLE 1

Androgen Receptor (AR) and DHT dependent transcription from the promoter of the probasin gene

| | Light Units ± std | | Fold Stimulation ± std | |
|---|---|---|---|---|
| DHT | pPBluc | pPBluc + AR | pPBluc | pPBluc + AR |
| control | 4200 ± 600 | 46000 ± 40000 | 1.00 ± 0.13 | 1.00 ± 0.08 |
| $10^{-9}$ M | 3000 ± 300 | 290000 ± 40000 | 0.71 ± 0.07 | 6.3 ± 0.9 |
| $10^{-7}$ M | 3300 ± 1100 | 1100000 ± 70000 | 0.78 ± 0.25 | 24 ± 1 |

CV1 cells were co-transfected with the probasin reporter gene (pPBluc) and with either the androgen receptor (pSGAR) or control plasmid (pSV2neo) and treated with vehicle or with DHT at the indicated concentration as described above.

EXAMPLE 5

Oral Composition

As a specific embodiment of an oral composition of a compound of this invention, 5 mg N-(4-chlorophenyl-(Z,Z) -2,3-bis(cyclopropylmethylene)cyclopentane carboxamide, is formulated with sufficient finely divided lactose to provide a total amount of 580 to 590 mg to fill a size 0 hard gelatin capsule.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method of treating or preventing diseases of the prostate comprising administering 0.001 to 200 mg per day of a compound capable of inhibiting androgen-induced DDT1 cell growth to a male human in need of such treatment wherein the compound is N-(4-chlorophenyl)-(Z, Z)-2,3-bis(cyclopropylmethylene)cyclopentane carboxamide of structural formula (I):

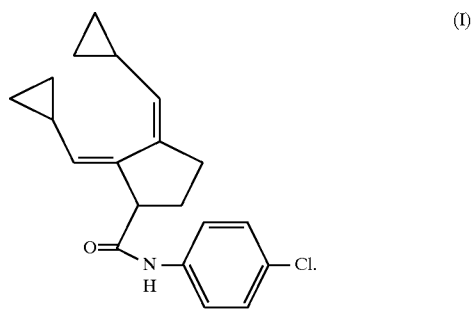

2. The method of claim 1 wherein the disease of the prostate is prostatic cancer.

3. The method of claim 1 wherein the disease of the prostate is benign prostatic hyperplasia.

4. A pharmaceutical composition for treatment of diseases of the prostate comprising N-(4-chlorophenyl)-(Z,Z)-2,3-bis (cyclopropylmethylene)cyclopentane carboxamide of structural formula (I):

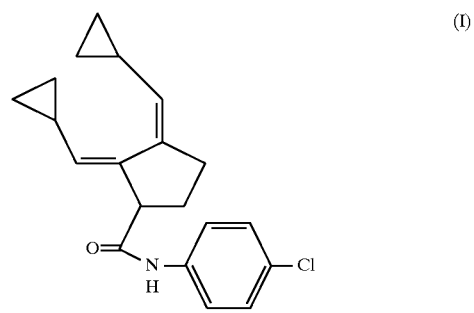

and a pharmaceutically acceptable carrier.

* * * * *